United States Patent [19]

Lange

[11] Patent Number: 5,442,293

[45] Date of Patent: Aug. 15, 1995

[54] METHOD AND APPARATUS FOR DETERMINING FLUID CONTENT AND CONDUCTIVITY IN POROUS MATERIALS

[76] Inventor: James N. Lange, Rte. 3 Box 212, Stillwater, Okla. 74075

[21] Appl. No.: 993,633

[22] Filed: Dec. 21, 1992

[51] Int. Cl.⁶ .................. G01V 3/08; G01V 3/10; G01V 3/12; G01R 27/02
[52] U.S. Cl. .................... 324/332; 324/696
[58] Field of Search ............ 324/332, 236, 654, 655, 324/694, 696

[56] References Cited

U.S. PATENT DOCUMENTS

| | | | |
|---|---|---|---|
| 3,870,951 | 3/1975 | Brown et al. | 324/61 P |
| 3,944,910 | 3/1976 | Rau | 324/6 |
| 4,156,177 | 5/1979 | Coates | 324/6 |
| 4,468,610 | 8/1984 | Hanson | 324/61 R |
| 4,850,386 | 7/1989 | Bireley | 137/78.3 |
| 4,929,885 | 5/1990 | Dishman | 324/664 |
| 4,991,915 | 2/1991 | Thompson et al. | 324/640 |
| 4,992,667 | 2/1991 | Abelentsev et al. | 250/390.05 |
| 5,039,947 | 8/1991 | Krazewski et al. | 324/634 |

*Primary Examiner*—Walter E. Snow

[57] ABSTRACT

A method and apparatus for determining the water content and its conductivity in porous media such as soils. The apparatus uses radio frequency electromagnetic fields to sample the environment of a sensor probe. One configuration uses an active oscillator including a sensor probe whose frequency of oscillation reflects the composite dielectric properties of the porous material in the vicinity of the sensor probe. A method which uses two sensor probes operating at different frequencies allows a quantitative determination of the water content and its conductivity. The apparatus has various configurations which allow it to evaluate fluid content in either unconsolidated or consolidated porous materials.

2 Claims, 4 Drawing Sheets

METHOD AND APPARATUS FOR DETERMINING FLUID CONTENT AND CONDUCTIVITY IN POROUS MATERIALS

BACKGROUND

Method and Apparatus for Determining Fluid Content and Conductivity in Porous Materials

1. Field of the Invention

This invention measures the fluid content and its conductivity in porous materials such as soils containing water in which solids are dissolved.

2. Description of Prior Art

This invention uses electromagnetic fields to investigate the fluid content of porous materials. For example, the water content of soil material is determined along with the conductivity of the water. The electromagnetic fields generated by the invention are affected by the dielectric polarizability and conductivity of the surrounding media. The net dielectric constant of porous materials is altered significantly by the presence of water since it has a large intrinsic dielectric constant (80) at the frequencies used in this invention, compared to the solid porous matrix, the dielectric constant of which is typically in a range from 2 to 7. When water fills the pores in the solid matrix the average dielectric constant of the combination changes significantly. For example, the dielectric constant for a typical dry soil (average composite of soil+air in pores) is approximately 3. However, if the pores are filled with water instead of air, the average dielectric constant for the water saturated soil can be as high as 23. When water does not completely fill the pores (partial saturation) the dielectric constant lies between 3 and 23. This large contrast in dielectric properties of dry and water-saturated soil significantly affects the penetration of electromagnetic fields. The decrease in electromagnetic field penetration as the moisture content increases is the means used to evaluate the water content of the porous material. In addition, through measurements made at different frequencies the conductivity of the water can be determined from known dispersion relations for dielectrics.

There are a number of prior methods to measure the water content of soils. One of the most common is gravimetric in which a sample of soil of known volume is removed and weighed. The soil is then placed in a drying oven and again reweighed until all the water has evaporated and the dried weight no longer changes. Using the weight difference between the wet and dry soil sample and the known density of water, the volume of water loss can be calculated. This method is intrusive since it requires the removal of soil and cannot be used to monitor changes in the same place as a function of time which might result from evaporation, rain migration, or evapotranspiration from the root zone of plants. The time required to take the measurement and the accuracy of the volume measurement preclude its application to long term monitoring of water content depth profiles.

Another common technique to measure water content involves electric measurements of buffed gypsum blocks. Their conductivity changes as they absorb water from their surroundings, but their placement disturbs the soil and their response varies with soil type making them very site-specific. The conductivity of the gypsum blocks is also affected by extraneous conductivity components such as fertilizer and other soluble components in the water. The long term calibration is affected by biological growth as well as changes in conductivity in soil water.

Another technique uses fundamental interactions between nucleons to measure the presence of water in porous media. This method employs the scattering of neutrons by the hydrogen in water. The neutron source contains a radioactive isotope which requires specific safety precautions. The neutron scattering length is over 25 cm in dry soils so measurement averages over a volume approximately 25 cms in radius. This volume average does not lead to a high resolution in the water content distribution and little definition of variation in water content in regions of interest in agriculture such as the root zone of plants. The neutron scattering method also does not discriminate between hydrogen in water and organic matter or some types of clay so that certain environments limit the accuracy of the measurements.

The U.S. Pat. No. 3,944,910 of R. N. Rau teaches a technique where microwave electromagnetic fields are emitted into the surroundings and used to detect the average dielectric constant from which the water content of earth formations of interest in geophysical prospecting can be determined. The use of high frequencies (>1GHz) in the microwave range means the energy does not penetrate very far into the surrounding media (approximately 1 to 2 cm). In the application described by Rau, the earth formation (consolidated rock) in the immediate vicinity of a borehole would be sampled. This is a region saturated by tiltrate from the drilling mud used to drill the borehole. The object of the microwave measurement is to determine water content and compare it with porosity measured by other techniques such as neutron scattering which does not differentiate between water and oil (hydrocarbon). The amount of pore volume not occupied by water is determined from the difference in the two measurements and is inferred to contain oil or gas. The intent of the measurement is to deal with fully saturated zones only in the immediate vicinity of the borehole to get an estimate of oil saturation and thus the use of high frequencies. The small penetration depth due to the high frequencies limits its use in sampling unaffected porous media such as soil. The apparatus has an antenna which uses a re-entrant cavity to radiate energy into the formation with a second re-entrant cavity as a receiver. The receiver is placed a significant distance from the transmitter, leading to a limited resolution of vertical changes in moisture content.

This technique of Rau's is limited to the region close to the borehole wall which it samples. This method does not yield a clear definition of the region it is sampling since there are multiple propagation paths shown in the patent. Because of the idamental size of the cavities and electronics, the borehole needed to insert the probe typically is over 15 cm in diameter, which is a significant intrusion for soil measurements. The method of evaluating either the porosity or saturation assumes that the formation is fully saturated with pore fluid. This is not independently verifiable and may not always occur, particularly if natural gas is present.

In a similar U.S. Pat. No. 4,158,165 of Coates, the formation properties are determined using a propagating microwave field around a borehole. Assuming that the infiltrated pore fluid has the same conductivity as the drilling fluid, water content is sought by measuring the microwave attenuation and phase shift. This assumption is not necessarily true when the formation contains orthogenic clays which interact with dissolved ions in the drilling fluid. To quantitatively determine the water content both Rau's and Coates' techniques require subsidiary assumptions which are not always strictly valid.

The U.S. Pat. No. 3,870,951 by Brown et. al. describes a probe which is designed to measure moisture in porous materials using a cylindrical capacitor terminating a coaxial cable. A separate cable is used to carry high frequency energy to the cylindrical capacitor. The measuring technique senses the change in the dielectric constant of the environment leading to a change in the terminating impedance in the receiving system. A DC voltage is generated which is proportional to the change in impedance of the circuit. No method is proposed to determine quantitatively the moisture content in the environment of the probe. Only relative changes are considered. The cylindrical capacitor which is the sensing unit for the moisture measurement necessarily restricts its electromagnetic field to a small region in the gap between the cylinders forming the capacitor. Therefore, it does not measure a significant lateral distance into the surrounding soil.

OBJECTS AND ADVANTAGES

The present invention is directed to a method and apparatus for determining fluid content, and conductivity particularly for water in porous media such as soils. The apparatus uses radio frequency electromagnetic fields to probe the porous media surrounding a sensing element. The sensing element forms a resonance circuit and is incorporated into an oscillator which includes an amplifier. The frequency of the oscillation varies with the dielectric constant and conductivity of the surrounding porous material which, in turn, is sensitive to the amount and conductivity of the water filling the pores. A measurement of the oscillation frequency is used to determine the fraction of pure water in the porous material. If the water contains dissolved components in solution and thus is conductive, a second coil operating at a different frequency than the first is used in determining the conductivity of the water in the pores. Evaluation of the measurements done at the two frequencies uses well-known dispersion relations for an electrolyte to obtain the conductivity of the pore fluid.

The dielectric response of the porous material to the imbibing of fluid has been determined empirically to proceed in a regular manner obeying a set of relationships determined by the experimental results. An important feature of soil responses to fluid saturation is that its dielectric properties are almost independent of the soil type.

The fundamental measurement of water content requires the determination of the composite dielectric constant of the porous media and fluid surrounding the probe. Using the measured composite dielectric constant in empirical equations yields the pore water content of the porous media. The evaluation procedure requires calibration of the apparatus to convert the measured quantity which is frequency to a physical property related to its surroundings (soil+water) which is the composite dielectric constant.

The calibration procedure consists of immersing the sensor probe into an unconsolidated porous material of known components. These may include liquids of well known dielectric constants or combinations of solids such as fused silica spheres fully saturated with a fluid whose dielectric properties are well known. The composite dielectric constant of this combination can be computed independently from known properties of the components. The resulting composite dielectric constant is used to calibrate the relationship between the frequency of the probe and surrounding dielectric properties. The fused silica spheres and calibration fluid comprise a physical system which is close to the physical properties of the soils in which the apparatus is designed to operate. This provides a realistic calibration procedure for the probe.

The calibration procedure is done with a variety of fluids saturating the porous fused silica matrix to provide a wide range of dielectric constants in order to mimic the range found in soils. This calibration procedure provides a quantitative relationship between the composite dielectric constant of the media surrounding the probe and the oscillation frequency of the probe. The water content is obtained from the empirical equations by substituting the value for the composite dielectric constant determined from the calibration relationship and frequency of operation of the sensor probe and electronic system.

This approach can be used to measure the water content in regions about a number of coils if the water is not conductive. The water content at various depths can be evaluated using one insertion shaft with a number of sensor coils. When the water is conductive this same apparatus can be used to determine both the water content and conductivity in a small region of soil. Coils of sufficiently differing frequency must be paired close to one another along the probe shaft. The conductive component in the water can result from such diverse sources as fertilizer, dissolved pollutants from a landfill, or saltwater intrusion. The conductivity is related to the number of dissolved ions which are present in the volume of water.

A procedure to calculate the conductivity of the water as proposed by Rau in U.S. Pat. No. 3,944,910 uses the attenuation of the electromagnetic field to determine the conductivity of the water. This approach is most effective at large conductivities and concentrations of water as found in formations saturated by drilling fluids. This approach does not work well when either the water content or its conductivity is low.

Another method which is taught in this patent to determine both the water content and its conductivity uses at least two measurements at different frequencies. The conductivity of the water introduces a dispersion (frequency dependence) in the dielectric constant of an electrolyte consisting of water containing dissolved ions. The dispersion of water as an electrolyte is given by $$\epsilon_w = \frac{\epsilon_0}{2} \left[ \sqrt{1 + \left(\frac{2\sigma}{f\epsilon_0}\right)^2} + 1 \right] \quad (1)$$

where f is the frequency, $\sigma$ is the conductivity and $\epsilon_0$ is the dielectric constant of water with no conductivity ($\epsilon_0 = 78$ at 20° C.). The dielectric constant of water containing soluble components decreases as the frequency increases. By calculating the dielectric constant of the water in the formation at two or more frequencies, both the amount and conductivity of the water can be determined by using equation 1. If the water is not conductive, the two measurements will yield the same value for the water content. When the two measurements lead to differing composite dielectric constants, the measurements can be fitted to the dispersion relation for an electrolyte, Eq. 1, and the volume and conductivity of the water determined.

REFERENCE NUMERALS IN DRAWINGS 1 sensor probe
3 rigid shaft
5 handles used to force penetration in unconsolidated porous materials
7 container enclosing electronics
9 hardened pointed tip for penetration into unconsolidated porous materials
11 protective sheath for coils 13
13 helical conducting coil
15 coil form
17 center conductor of a coaxial cable
19 insulating sheath of a coaxial cable
21 outer conductor of a coaxial cable
23 conducting connection between the coil and center conductor of the coaxial cable
25 surface tangent to the electromagnetic field configuration generated by the sensor probe 1
29 amplifier
31 feedback network
33 sweep oscillator
35 directional coupler
37 power law or amplitude detector
39 analog to digital conversion circuit
41 microprocessor unit
42 read-only memory containing evaluation software
43 digital input/output data bus
45 display panel
47 transistor or integrated circuit amplifier
49 automatic gain control circuit
51 frequency counter
53 phase locked loop integrated circuit
55 operation amplifiers used to determine a voltage difference
57 reference voltage generated by an operational amplifier
59 random access memory
60 frequency value for a sensor probe oscillator as determined by circuits in FIG. 5, 6, or 7
61 an equation whose coefficients are determined empirically from the calibration procedure
62 dielectric constant of material surrounding the sensor probe
63 the water content calculated by inserting the frequency into the calibration equation
65 equation based on empirical calibration
67 effective dielectric constant of an electrolyte
69 dispersion law for electrolytes
71 net conductivity of the formation
73 mixing law for a composite dielectric material
75 conductivity per unit volume of water

DESCRIPTION OF THE INVENTION

Figure 1:
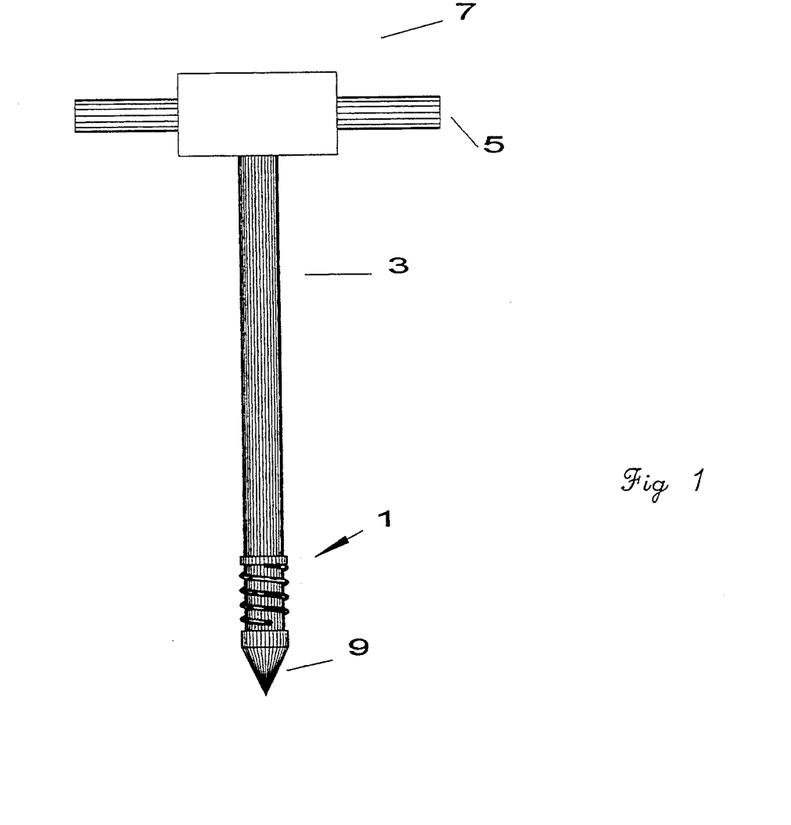
FIG. 1 shows an overall view of one embodiment of the apparatus.

The apparatus in FIG. 1 contains an electrically reactive system which is used with an electronic feedback amplifier to form a self-sustained oscillation. The reactive component consists of an ungrounded sensor probe 1, and a length of coaxial cable. The coaxial cable connects the sensing coil through the rigid support shaft 3 to the electronics system and power source at the top of the device 7. The apparatus is sensitive to the composite dielectric constant of the porous media through the penetration of the electromagnetic fields emitting from the sensor coil as alternating currents are generated by the oscillator. The frequency of the oscillator is determined by such quantities as the number of turns of the sensor probe 1, and the length of coaxial cable in addition to the composite dielectric constant of the partially saturated soil. All of these quantities are fixed in constructing the apparatus and the insertion hole and are present during the calibration outlined above. Changes in frequency of the oscillator resulting from insertion into the ground are related to the water content of the soil.

Figure 2:
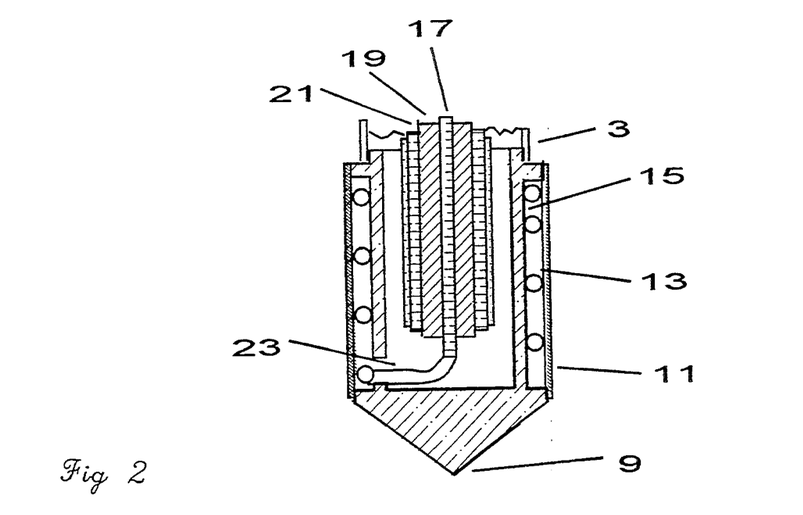
FIG. 2 shows a crossectional view of the sensor probe showing the ungrounded coil with a connection to a coaxial cable inside the shaft.
Figures 3, 4:
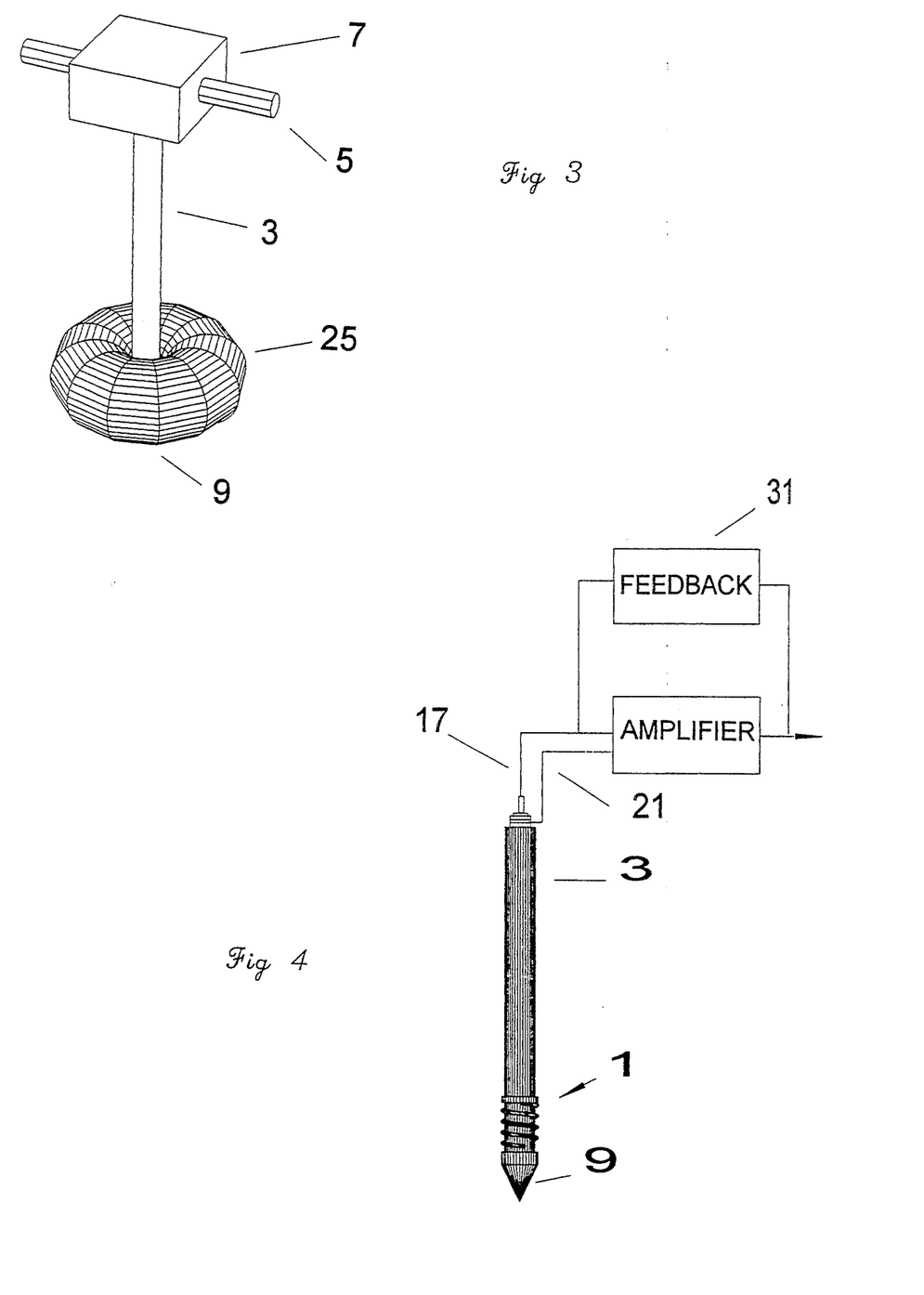
FIG. 3 shows a representative electromagnetic field shape generated by the sensor probe and electronics of the apparatus.
FIG. 4 shows a block diagram of the oscillator circuit including the coaxial line and sensor probe.

The electromagnetic fields which emanate from the sensing probe 1 are primarily a function of its geometry. The details of the sensing probe are shown in FIG. 2. One end of an electrically conducting coil 13 is connected to the center conductor of the coaxial line 17 through 23 while the other end of the coil is not grounded. This electrical connection arrangement along with the distance between the windings of the coil is designed to maximize the electromagnetic fields external to the center of the coil. This enhances the volume which is sampled in the exterior soil region. The configuration of the external field is represented in FIG. 3 by a surface 25, drawn along the field lines. The surface is determined empirically from the position at which a dielectric with a dielectric constant of twice that of soil would be placed to get a 1% decrease in frequency of the oscillator. The surface 25, is roughly in the form of a donut with an exterior radius six times the coil diameter. For a typical coil operating at radio frequencies (100 MHz) the exterior radius of the donut is 7 cms. The extent and shape of this surface which bounds the volume of soil sensed by the electromagnetic fields of the sensor is primarily dependent on the geometry and dimensions of the coil with added affects due to the position of the coaxial line and support shaft. The sensing volume of the coil can be adjusted empirically to satisfy the particular resolution needs.

The apparatus described above has a number of applications in both consolidated and unconsolidated porous materials using different sensing coil geometries. For unconsolidated materials such as soil where a volume is sampled, the sensing probe is inserted directly into the material or alternatively it is moved in a casing tube in an insertion hole. The sensing element can be a helix as shown in FIG. 1 where the length and coil separation (pitch) affect the soil volume sampled and frequency of oscillation. Another coil form used in direct insertion can be a quadrapole or baseball winding coil. This yields a fundamentally different form of winding and electromagnetic field configuration than the helix. For consolidated porous materials the sensing element cannot be inserted directly into the porous material but is restricted to measurements from the free surface. The coil is arranged primarily in an array such as a spiral or a balanced butterfly configuration. For unconsolidated materials coil array conforms to the surface contour, i.e., a flat coil for a planar surface or a segment of a cylinder for inside a cylindrical bore hole. The sampling volume of the porous material is a region directly below the plane of the coil extending through the surface of the consolidated porous media. Both the coils designed for direct insertion and those used for surface scanning are ungrounded electrical configurations attached to a coaxial conductor or similar two conductor lines.

An arrangement of a number of coils at different positions along the insertion shaft 3 allows simultaneous detection of the water content at various depths. Each coil is fabricated to operate in a different frequency range and is attached to its own coaxial line to form the reactive component of a separate oscillator. Because the detectors operate at different frequencies, their frequency changes with moisture content do not interfere and the information each produces is characteristic of its predetermined insertion depth. The multiple coil configuration may contain many sensors inserted at various depths in the soil to monitor water migration over extended periods of time.

Figure 5:
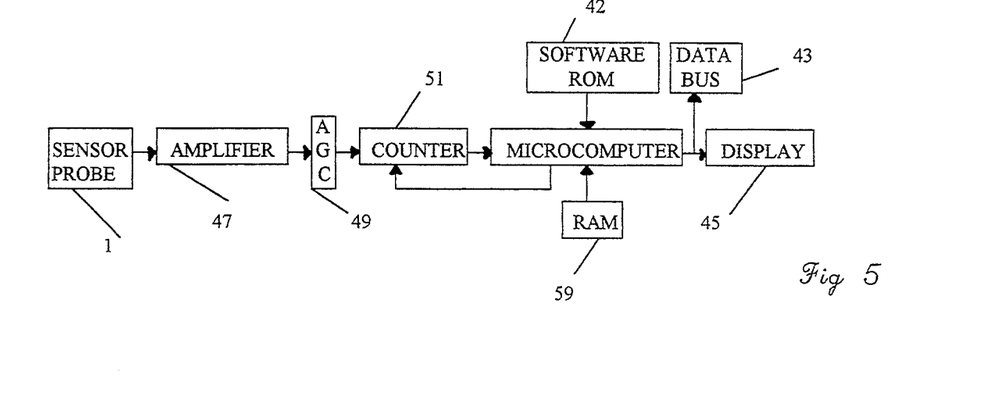
FIG. 5 shows a block diagram of the arrangement of a primarily digital electronic measuring circuit with the sensor probe combined in an active oscillator shown in FIG. 4.

The active unit in the apparatus is an oscillator formed by the sensing coil and its environment in combination with an amplifying stage containing feedback. The electronic arrangement is shown in FIG. 4 where the sensing probe system 1 is attached to an amplifying stage of either a differential input video amplifier 29 or a transistor. The combination forms an oscillator the frequency of which is related to the composite dielectric constant of the material surrounding the sensor coil. The frequency of oscillation can be determined by a frequency counter 51 which is coupled to a microprocessor 41 as shown in FIG. 5. The calibrated frequency response of the sensing coil as a function of the composite dielectric constant of its surroundings is contained in software in a memory device the microprocessor can access. The read only memory 42 contains a software program which applies the calibration to the averaged frequency of the oscillator to yield a value for the water content. The resulting digital value is interpreted by an electronic circuit to display the value of the water content calculated by the software using information from the calibration procedure. The calculated values can be accessed in random access memory 59 through a data bus. Additional information included in the random access memory could include the position of the site and depth, date, and time of measurement.

Figure 6:
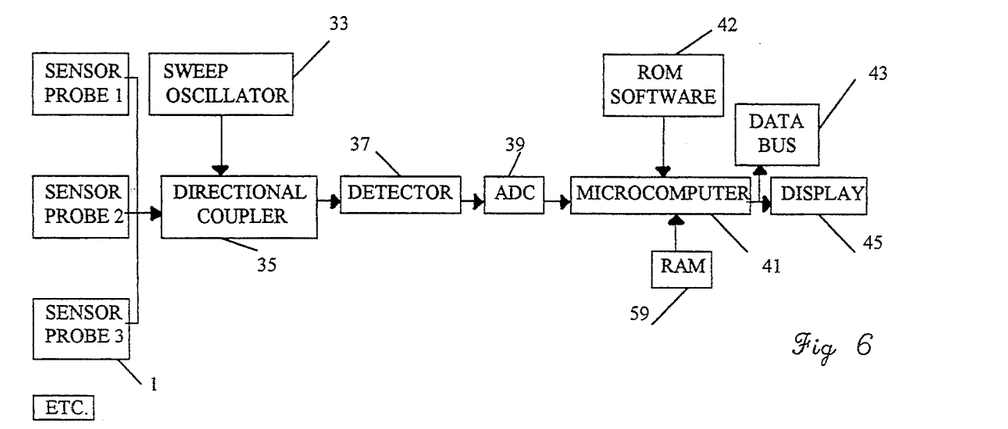
FIG. 6 shows a block diagram of an electronic arrangement designed to measure the properties of the sensor probe using a sweep oscillator rather than the active oscillator shown in FIG. 4.
Figure 7:
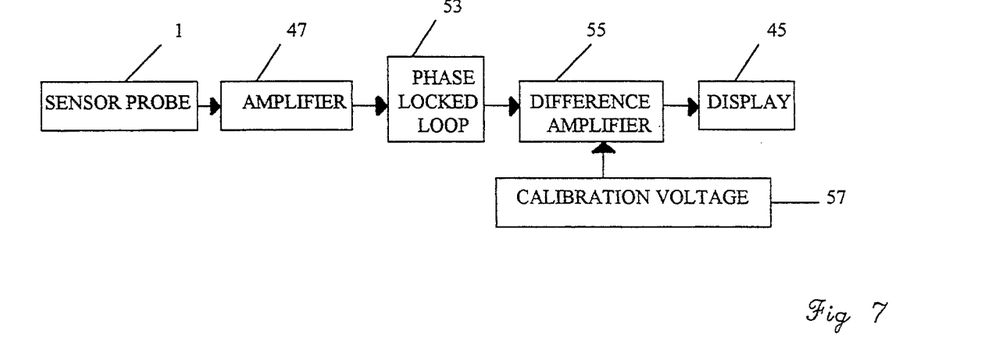
FIG. 7 shows a block diagram of an analog electronic measuring circuit using the active oscillator shown in FIG. 4.

Another configuration for the apparatus is shown in FIG. 6 in which a number of coils are connected to a single coaxial cable using a mechanical or electronic switch. The resonance frequency of each coil is made different by adjusting the size and shape of the coils. The coils may be placed close together to detect water content and conductivity in a small lateral strata of soil or broadly spaced to monitor water content profiles with depth. The electrical response of the coils is detected by a network using a directional coupler 35 and sweep oscillator 33. The oscillator changes its frequency as a function of time but at a constant amplitude. The energy reflected from the coil circuit is directed by the directional coupler to the detector 37. The resonance frequency of the coil is detected as a minima in the frequency response of the network. The microprocessor 41 controls the frequency of the sweep oscillator while detecting the amplitude of the reflected energy. It uses prestored software 42 to evaluate the amplitude as a function of frequency to identify at which frequency the minima occur and thereby determine the resonance frequency of each of the sensor coils. Additional software applies calibration information to the results so that a conversion value of the frequency to water content at each depth can be displayed. An electronic arrangement using exclusively analog components as in FIG. 7 can also be used to determine the relevant parameters to evaluate the water content.

OPERATION

The method for determining the water content in the porous material is a two step process. The first step is the measurement of the frequency of oscillation of the probe system using the apparatus shown in FIG. 1 or a similar configuration. The frequency of oscillation of the sensor probe is converted to dielectric constant by calibrating the frequency response of the sensing probe in known dielectric environments. This calibration procedure uses the relationship between the composite dielectric constant of the known mixture as discussed above. The response frequency of the sensing probe is converted to the composite dielectric constant of the porous material surrounding the probe using the results of the calibration procedure. Determination of the composite dielectric constant of the media surrounding the probe is the first step in the evaluation process. The second step in the process of evaluating the water content depends on whether there are any dissolved ions in the pore water to lead to significant electrical conductivity resulting in dispersion of the dielectric constant. When the pore fluid has no or little conductivity the following is the appropriate procedure.

Figure 8:
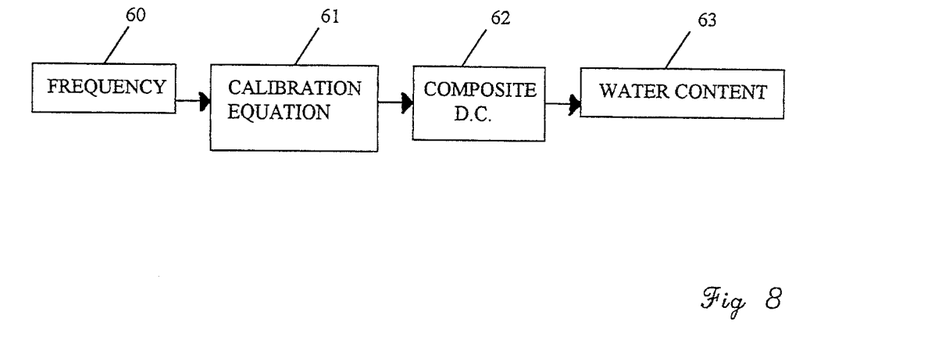
FIG. 8 shows a block diagram of the evaluation procedure embodied in computer software used to compute water content when no conductivity is present.

The composite dielectric constant (Ec) determined from the frequency of oscillation of the probe is substituted into empirical relationships which yield the water content when the fluid is non-conductive. The empirical equations have been shown to be independent of specific soil type by different investigations. For the lower saturations, the water content ($\theta$) is given by $$\theta = 0.128 \sqrt{\epsilon_c} - 0.204 \qquad (2)$$

at higher water contents another equation applies which is given by $$\theta = 0.011 \epsilon_c + 0.796 \qquad (3)$$

Where $\epsilon_c$ is the composite dielectric constant measured by the calibrated probe. The relationship used to determine the water content for intermediate saturations is either equation 3 or 4, whichever yields the lower water content. The procedure is shown in the block diagram of FIG. 8 for non conducting pore fluids.

The second step in the fluid content evaluation procedure outlined above is altered when there is appreciable conductivity in the water contained in the pores. The altered procedure requires more than one measurement of the surrounding dielectric constant at different frequencies. The two or more measurements use sensing probes operating at different frequencies in the range from 0.1 MHz to 200 MHz. When the water contains dissolved ions to form an electrolyte, the dielectric constant varies with frequency in a manner outlined above in equation 1. The first step of the procedure is the same as that for non conductive water. The composite dielectric constant of the porous media and conducting fluid surrounding the various sensing probes operating at different frequencies is determined using the calibration between probe frequency and dielectric constant. If the water is conductive the composite dielectric constant is not the same at different measuring frequencies. The difference in the dielectric constant at two frequencies indicates that the evaluation procedure must be altered from the second step used for non-conductive pore water to a new procedure.

Figure 9:
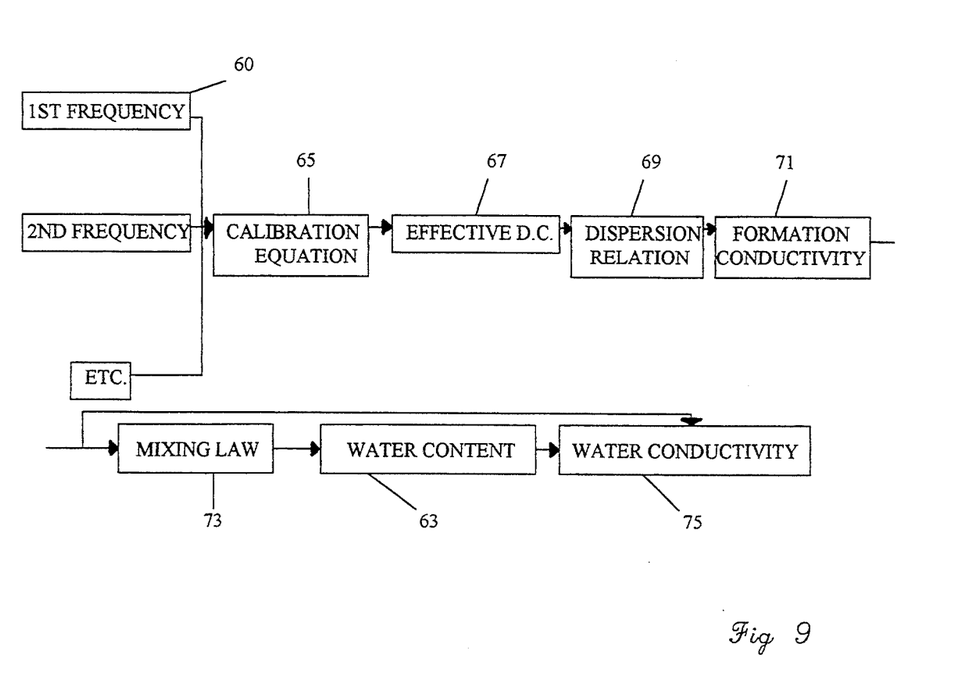
FIG. 9 shows a block diagram of the computer software used to find the conductivity per unit volume and the water content using measurements at two or more frequencies.

In the new procedure outlined in FIG. 9, the different values of the composite dielectric constant are used with the electrolyte dispersion relation to determine the water content and conductivity of the fluid. If as in FIG. 4 two different coil sizes are used they will yield differing composite oscillator frequencies f and f'. When the water is an electrolyte containing dissolved ions, two different values of composite dielectric constant $\epsilon_c$ and $\epsilon_c'$ will be measured for the same water content. The dispersion relationship for the electrolyte (Eq. 1) is used with the appropriate dielectric mixing laws to yield a set of equations which allow computation of the conductivity $\sigma$ of the pore water. When the conductivity of the water is large (i.e. $\sigma > 0.1$ mhos/m at 100 MHz.) an approximate equation for the conductivity can be written as $$\sigma = \frac{\epsilon_0(\epsilon_c - \epsilon_c')}{2\left[\frac{(\epsilon_c' - B)}{f'} - \frac{(\epsilon_c - B)}{f}\right]} \quad (4)$$

where $\epsilon$ and $\epsilon'$ are measured at two different frequencies f and f' and B is 2.80. The value of the pore water conductivity derived from this equation is used with the dielectric dispersion relation and mixing laws to determine the water content. If no significant conductivity is present, the two measurements at f and f' yield the same composite dielectric constant.

The second relationship derived from the dispersion relation Eq. (1), uses the measured values of the composite dielectric constant value ($\epsilon_c$) and pore water conductivity to obtain the water content $\theta$. The conductivity of the water ($\sigma$) obtained from equation 4 is used with the dispersion relation (Eq. 1) the measured composite dielectric constant $\epsilon_c$ and a simple additive mixing law to obtain the water content as $$\theta = \frac{\epsilon_c' - B}{\epsilon_w'} \quad (5)$$

where B is a constant given approximately by B=2.80.

The finite conductivity $\sigma$ reflects the presence of soluble components in the pore water. The magnitude of the pore water conductivity is an important parameter, for example, in observing the movement of water soluble pollutants in the soil. A determination of the pollutants' movement is presently not possible without severe intrusion. The measurement procedure for electrolytes is diagrammed in FIG. 9. Using this procedure, long term monitoring of the movement of soluble pollutants from landfills is possible before they reach aquifers. This method and apparatus allows monitoring of the movement and fate of pollutants in unsaturated soils over long periods without significant intrusion. This type of monitoring is not practical on a large scale using other techniques.

Although the description above contains many specificity's, these should not be construed as limiting the scope of the invention but as merely illustrations of some of the presently preferred embodiments of this invention. For example, the sensing coil may have other shapes such as conical or spherical, etc.; The number and arrangement of the coils on the shaft may occur in groups of irregular spacing; the electronic circuits may consist of large-scale integrated circuits which combine and enhance electronic and computational functions. Thus, the scope of the invention should be determined by the appended claims and their legal equivalents, rather than by examples given.

CONCLUSION, RAMIFICATIONS, AND SCOPE

The present invention is able to monitor the water content of soils and other porous materials such as grain or construction cement over extended periods of time. Some embodiments are designed to measure the volume distribution of water by inserting the sensing element into the unconsolidated porous media. Other embodiments are configured to measure the water content immediately below the surface in consolidated porous materials such as lumber. Determinations of both fluid content and conductivity are done using measurements at different frequencies using embodiments with multiple sensing probes of differing geometries.

This invention has application to unique problems which are presently difficult to solve including the most efficient use of water in irrigation which requires knowledge of the water content distribution in the root zone of plants. This invention provides a high resolution depth profile which can enhance water conservation. Another application is the determination of migration patterns of soluble components of polluting effluent from landfills. This invention is able to follow the pollutant migration in the soil and determine its fate by making repeated water content and conductivity measurements with depth to provide soil water/effluent concentration profiles. There is presently no reliable way of following pollutant migration in unsaturated soils before they reach the water table. Another application of this invention is to evaluate the structural fatigue of composite graphite epoxy structures by using a surface probe. Water which leaches into cracks resulting from delaminations can be detected from the surface using this invention. The amount of water indicates the extent of structural degeneration in the composite material.

I claim:

1. An apparatus for measuring fluid content and pore fluid conductivity in unconsolidated porous media of known composition and fluid type comprising:

a hollow cylindrical element constructed of dielectric material surrounding an axial bore, a plurality of electrically conductive wires each wound in the approximate form of a helix on the exterior surface of said hollow cylindrical element of elliptical crossection with coincident symmetry axes of rotation and supported thereby and placed axially along said hollow cylindrical element, a sealing means on the surface of each said helix, a plurality of coaxial conducting cables positioned within the axial bore of said cylindrical element of elliptical crossectional for connection to each said helix, whereby the center conducting wire is connected and no connection is made to the outer conductor of said coaxial cable, a circuit means connected through a switching means to one end of said coaxial cable and said helixes connected to the other end of said coaxial cable, to establish an electric field through the materials surrounding the apparatus in order to polarize the porous media and it's contained fluids, said coaxial cable, helixes and surrounding material form an electrical resonance composite circuit which is connected remotely by both leads of the coaxial cable to a detector circuit whereby the self resonance frequency and amplitude response of said composite circuit is determined quantitatively and each helix having a different number of revolutions whereby the self resonance frequency of each coil is different from the others, and a detector circuit to determine each of said probes' natural frequency and amplitude response.

2. An apparatus for measuring fluid content and pore fluid conductivity in consolidated porous media:

a plurality of probes aligned parallel to a curved surface and adjacent to each other, each of said plurality of probes comprising:

a curved disc element constructed of dielectric material surrounding an axial bore, an electrically conductive wire wound in the approximate form of a spiral on the exterior curved planar surface of said disc element with coincident axes of rotation and supported thereby, on the surface of said spiral, a sealing means on the surface of each said spiral, a coaxial cable for connection to each of said plurality of probes, whereby the center wire is connected and no connection is made to the other conductor of said coaxial cable, a circuit means connected through a switching means to one end of said coaxial cable and wire spirals connected to the other end of said coaxial cable to establish an electric field through the material surrounding the apparatus in order to polarize the porous media and it's contained fluids, said coaxial cable, spiral wire and adjacent consolidated porous material form an electrical resonance composite circuit which is connected remotely to a detector circuit whereby the self resonance frequency and amplitude response of said composite circuit is determined quantitatively, said probes, each having a different number of revolutions in the said spiral winding whereby the self resonance frequency of each coil is different from the others, and a detector circuit to determine each of said probes' natural self frequency and amplitude response.

* * * * *